United States Patent
Yoon et al.

(10) Patent No.: US 6,762,189 B1
(45) Date of Patent: Jul. 13, 2004

(54) 5-PYRIMIDINECARBOXAMIDE DERIVATIVES AND THE PHARMACEUTICAL COMPOSITIONS CONTAINING SAID DERIVATIVES

(75) Inventors: Sung June Yoon, Seoul (KR); Sang Wook Lee, Kyunggi-do (KR); Nam Doo Kim, Inchon-si (KR); Yong Kyun Park, Kyunggi-do (KR); Geun Hyung Lee, Kyunggi-do (KR); Jong Woo Kim, Kyunggi-do (KR); Sang Jin Park, Seoul (KR); Hee Jeoung Park, Kyunggi-do (KR); Hwan Bong Jang, Inchon-si (KR)

(73) Assignee: Dong Wha Pharm. Ind. Co., Ltd. (KR)

( * ) Notice: Subject to any disclaimer, the term of this patent is extended or adjusted under 35 U.S.C. 154(b) by 40 days.

(21) Appl. No.: 10/148,491

(22) PCT Filed: Nov. 27, 2000

(86) PCT No.: PCT/KR00/01364

§ 371 (c)(1),
(2), (4) Date: May 24, 2002

(87) PCT Pub. No.: WO01/38308

PCT Pub. Date: May 31, 2001

(30) Foreign Application Priority Data

Nov. 27, 1999 (KR) ......................................... 1999-53294
Dec. 29, 1999 (KR) ......................................... 1999-64402

(51) Int. Cl.$^7$ .................... C07D 239/10; C07D 213/72; A61K 31/506; A61P 31/12; A61P 31/18

(52) U.S. Cl. ...................... 514/274; 544/317; 548/362.1
(58) Field of Search ............................ 514/274; 544/317

(56) References Cited

FOREIGN PATENT DOCUMENTS

| WO | WO 98/54140 | 12/1998 |
|----|-------------|---------|
| WO | WO 99/58526 | 11/1999 |

OTHER PUBLICATIONS

Sarbath et al., J. Clin. Gastroenterol. 30(2) 125–143, 2000.*
Brisibe et al., Trends Biotechol. 21(7): 306–311, 2003.*

* cited by examiner

*Primary Examiner*—Venkataraman Balasubramanian
(74) *Attorney, Agent, or Firm*—Muserlian, Lucas & Mercanti, LLP

(57) ABSTRACT

The present invention relates to novel 5-pyrimidinecarboxamide derivatives and the pharmaceutical compositions containing said derivatives, and more specifically, to 5-pyrimidinecarboxamide derivatives and their pharmacutically able salts, the process for preparing them, and the pharmaceutical compositions containing said compounds as active ingredients. In particular, said 5-pyrimidinecarboxamide derivatives of the present invention, due to their inhibitory activity against the proliferation of human immunodeficiency virus (HIV) as well as hepatitis B virus (HBV), can be used as a therapeutic agent as well as a preventive agent for hepatitis B and acquired immune deficiency syndrome (AIDS).

4 Claims, No Drawings

5-PYRIMIDINECARBOXAMIDE DERIVATIVES AND THE PHARMACEUTICAL COMPOSITIONS CONTAINING SAID DERIVATIVES

This patent application claims a benefit of priority from Korean Patent Application No. 1999/53294 filed Nov. 27, 1999 and Korean Patent Application No. 1999/64402 filed Dec. 29, 1999 through PCT Application Serial No. PCT/KR00/01364 filed Nov. 27, 2000, the contents of each of which are incorporated herein by reference

TECHNICAL FIELD

The present invention relates to novel 5-pyrimidinecarboxamide derivatives and the pharmaceutical compositions containing said derivatives. More specifically, the present invention relates to novel 5-pyrimidinecarboxamide derivatives and their pharmaceutically acceptable salts represented below in formula 1, which have excellent inhibitory effect on proliferation of hepatitis B virus and of human immunodeficiency virus. The present invention also relates to the process for preparing compounds of formula 1 and to the pharmaceutical compositions containing said derivatives as effective ingredients against viruses.

Formula 1

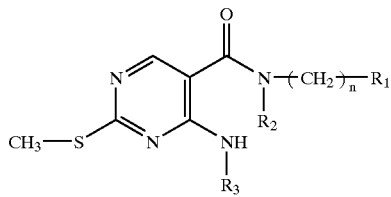

Wherein, $R_1$ is H, hydroxy, straight or branched alkyl group with $C_1$~$C_5$, straight or branched alkoxy group with $C_1$~$C_5$, straight or branched hydroxyalkyl group with $C_2$~$C_6$, dialkylamino group with $C_2$~$C_6$ straight or branched alkyl group with $C_2$~$C_6$ substituted with hydroxy or alkoxycarbonyl group with $C_2$~$C_5$, cycloalkyl group with $C_3$~$C_6$, or saturated or unsaturated 5 or 6 membered heterocyclic compounds containing 1 to 3 heteroatoms selected from N, O, and S, which may be unsubstituted or substituted with alkyl group of $C_1$~$C_3$; $R_1$ may or may not contain asymmetrical carbons;

$R_2$ is H or straight or branched alkyl group with $C_1$~$C_4$; Or both $R_1$ and $R_2$ consist of 5 or 6 membered saturated heterocyclic ring containing 1~3 heteroatoms selected from N, O, and S, which is unsubstituted or substituted with straight or branched alkyl group with $C_1$~$C_5$ or straight or branched hydroxyalkyl group with $C_2$~$C_5$;

n is an integer between 0 and 4;

$R_3$ is indazol-5-yl, or indazol-6-yl.

BACKGROUND ART

Hepatitis B virus (HBV; referred as "HBV" hereinafter) causes acute or chronic hepatitis, which may progress to liver cirrhosis and liver cancer. It is estimated that three hundred million people are infected with HBV in the world (Tiollais & Buendia, Sci. Am., 264, 48, 1991). There has been much research about the molecular biological characteristics of HBV and their relationship to liver diseases in order to find ways to prevent and treat hepatitis B. Various vaccines and diagnostic drugs have been developed and much effort is being channeled into research to find treatment for hepatitis B.

HBV genome consists of genes for polymerase (P), surface protein (pre-S1, pre-S2 and S), core protein (pre-C and C), and X protein. Of these proteins expressed from HBV genes, polymerase, surface protein, and core protein are structural proteins and X protein has a regulatory function.

The gene for HBV polymerase comprises 80% of the whole virus genome and produces a protein of 94kD size with 845 amino acids, which has several functions in the replication of virus genome. This polypeptide includes sequences responsible for activities of protein primer, RNA dependent DNA polymerase, DNA dependent DNA polymerase, and RNase H. Kaplan and his coworkers first discovered reverse transcriptase activities of polymerase, which led to much research in replicating mechanism of HBV.

HBV enters liver when antigenic protein on virion surface is recognized by hepatic cell-specific receptor. Inside the liver cell, DNAs are synthesized by HBV polymerase action, attached to short chain to form complete double helix for HBV genome. Completed double helical DNA genome of HBV produces pre-genomic mRNA and mRNAs of core protein, surface protein, and regulatory protein by the action of RNA polymerase. Using these mRNAs, virus proteins are synthesized. Polymerase has an important function in the production of virus genome, forming a structure called replicasome with core protein and pre-genomic mRNA. This process is called encapsidation. Polymerase has repeated units of glutamic acid at the 3'-end with high affinity for nucleic acids, which is responsible for facile encapsidation.

When replicasome is formed, (−) DNA strand is synthesized by reverse transcribing action of HBV polymerase and (+) DNA strand is made through the action of DNA dependent DNA polymerase, which in turn produces pre-genomic mRNAs. The whole process is repeated until the pool of more than 200 to 300 genomes is maintained (Tiollais and Buendia, Scientific American, 264: 48–54, 1991).

Although HBV and HIV are different viruses, the replication mechanisms during their proliferation have some common steps, namely, the reverse transcription of virus RNA to form DNA and the removal of RNA strand from subsequently formed RNA-DNA hybrid.

Recently, nucleoside compounds such as lamivudine and famvir have been reported to be useful inhibitors of HBV proliferation, although they have been originally developed as therapeutics for the treatment of acquired immune deficiency syndrome (AIDS; referred as "AIDS" hereinafter) and herpes zoster infection (Gerin, J. L, Hepatology, 14: 198–199, 1991; Lok, A. S. P., J. Viral Hepatitis, 1: 105–124, 1994; Dienstag, J. L. et al., New England Journal of Medicine, 333: 1657–1661, 1995). However, these nucleoside compounds are considered a poor choice for treatment of hepatitis B because of their high cost and side effects such as toxicity, development of resistant virus and recurrence of the disease after stopping treatment. Effort to find therapeutics for hepatitis B among non-nucleoside compounds has been continued and antiviral effects against HBV have been reported for quinolone compounds (EPO563732, EPO563734), iridos compounds (KR 94-1886), and terephthalic amide derivatives (KR 96-72384, KR 97-36589, KR 99-5100). In spite of much effort, however, effective drugs for treating hepatitis B have not been developed yet and therapeutic method mainly depends on symptomatic treatment.

AIDS is a disease inducing dramatic decrease in immune function in the body cells and causing various symptoms of infection rarely seen in normal human beings, which spread to the whole body. Human immunodeficiency virus (HIV; referred as "HIV" hereinafter) responsible for AIDS is known to mainly attack helper T cells, which is one of the T cells with regulatory function in the immune system. When helper T cells are infected with HIV virus and undergo necrosis, human immune system cannot function properly. Impairment in immune function subsequently results in fatal infection and development of malignant tumor. Since AIDS patient has been found in USA in 1981 for the first time, the number increased to more than 850,000 patients in 187 countries in 1993 (WHO 1993 report). WHO predicted that 30 to 40 million more people would be infected with HIV by the year 2000 and 10 to 20 million of them would develop the disease.

At the present time, drugs controlling proliferation of HIV have been most widely used for the treatment of AIDS. Of these, Zidovudine, which had been named Azidothymidine previously, is a drug developed in 1987. Didanosine was developed in 1991 as an alternative medicine for AIDS patients when Zidovudine was either ineffective or could not be used due to side effects. In addition, Zalcitabine was approved for concurrent use with Zidovudine in 1992. These drugs alleviate symptoms, slow down progression of the disease in the infected individuals to full-blown AIDS, and somewhat extend life span in the patients. These drugs, however, are not able to cure the patients completely and often develop problems such as resistance and side effects.

In light of these problems, we, inventors of the present invention, tried to develop therapeutics to treat hepatitis B with little chance of toxicity, side effects, and development of resistant viral strains. We found the compounds with excellent antiviral effect against HBV; synthesized novel 5-pyrimidinecarboxamide derivatives represented in formula 1 and completed the invention by showing their dramatic inhibitory effect on proliferation of HIV as well as of HBV.

DISCLOSURE OF INVENTION

The present invention provides novel 5-pyrimidinecarboxamide derivatives and the pharmaceutical compositions containing said derivatives. More specifically, the present invention provides 5-pyrimidinecarboxamide derivatives and their pharmaceutically acceptable salts, the process for their preparation and the pharmaceutical compositions containing said derivatives as effective ingredient. 5-pyrimidinecarboxamide derivatives of the present invention inhibit proliferation of hepatitis B virus as well as of human immunodeficiency virus and may be effectively used for prevention and treatment of hepatitis B and AIDS.

In order to accomplish the aforementioned goal, the present invention provides novel 5-pyrimidinecarboxamide derivatives represented below in formula 1 and their pharmaceutically acceptable salts.

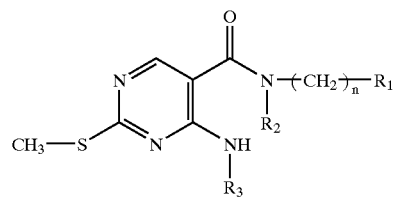

Formula 1

Wherein, $R_1$ is H, hydroxy, straight or branched alkyl group with $C_1$~$C_5$, straight or branched alkoxy group with $C_1$~$C_5$, straight or branched hydroxyalkyl group with $C_2$~$C_6$, dialkylamino group with $C_2$~$C_6$, straight or branched alkyl group with $C_2$~$C_6$ substituted with hydroxy or alkoxycarbonyl group with $C_2$~$C_5$, cycloalkyl group with $C_3$~$C_6$, or saturated or unsaturated 5 or 6 membered heterocyclic compounds containing 1 to 3 heteroatoms selected from N, O, and S, which may be unsubstituted or substituted with alkyl group of $C_1$~$C_3$; $R_1$ may or may not contain asymmetrical carbons;

$R_2$ is H or straight or branched alkyl group with $C_1$~$C_4$;

Or both $R_1$ and $R_2$ consist of 5 or 6 membered saturated heterocyclic ring containing 1~3 heteroatoms selected from N, O, and S, which is unsubstituted or substituted with straight or branched alkyl group with $C_1$~$C_5$ or straight or branched hydroxyalkyl group with $C_2$~$C_5$;

$R_3$ is indazol-5-yl or indazol-6-yl;

n is an integer between 0 and 4.

When both $R_1$ and $R_2$ are represented as a 5 or 6 membered heterocyclic compounds with 1 to 3 heteroatoms selected from N, O, and S, n equals 0. This heterocyclic ring may be unsubstituted or substituted with straight or branched alkyl group with $C_1$~$C_5$, straight or branched hydroxyalkyl group with $C_2$~$C_5$, or hydroxy group;

When $R_1$ in formula 1 contains asymmetrical carbons, they may exist as either R or S optical isomer and the present invention covers both optical isomers and the racemic mixture as well.

Indazol-5-yl and indazol6-yl groups for $R_3$ in the present invention are represented in formula 2 and 3 respectively.

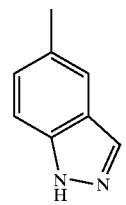

Formula 2

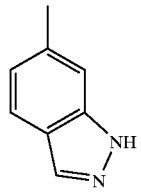

Formula 3

Compounds of formula 1 in the present invention may be utilized in the form of salts and the acid addition salts prepared by adding pharmaceutically acceptable free acids are useful. Compounds of formula 1 may be changed to the corresponding acid addition salts according to the general practices in this field. Both inorganic and organic acids may be used as free acids in this case. Among inorganic acids, hydrochloric acid, hydrobromic acid, sulfuric acid, and phosphoric acid may be used. Among organic acids, citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid and aspartic acid may be used.

Furthermore, the present invention provides a process for preparing 5-pyrimidinecarboxamide derivatives represented below in scheme 1.

2-B) Preparation of 5-pyrimidinecarboxamide derivatives of formula 1 by first hydrolyzing the compound of formula 6 synthesized in step 1 to form 5-pyrimidinecarboxylic acid derivatives of formula 8, then activating to Vilsmeier intermediate in the presence of N, N-dimethylformamide and $SOCl_2$, and allowing it to react with amine compound of formula 7.

Chemical agents used in scheme 1, namely, 4-chloro-2-methylthio-5-pyrimidinecarboxylic acid ethyl ester of formula 4, 5-aminoindazole or 6-aminoindazole of formula 5, and amine compound of formula 7 are commercially available and may be purchased easily.

The process of preparing compounds of formula 1 is described in more detail in the following.

For the reaction of 4-chloro-2-methylthio-5-pyrimidinecarboxylic acid ethyl ester of formula 4 with

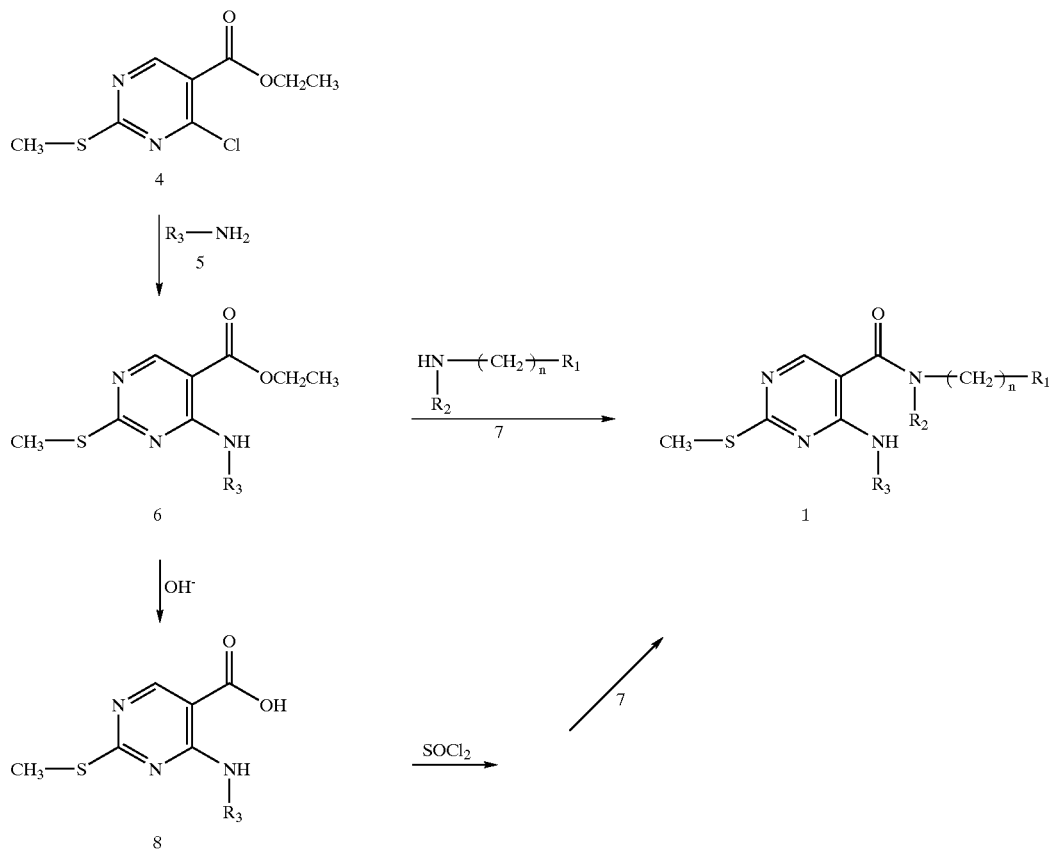

Scheme 1

Wherein, $R_1$, $R_2$, $R_3$ and n are as defined in formula 1.

The process of preparing compounds of formula 1 in the present invention comprises two steps as in the following:
1) Preparation of 5-pyrimidinecarboxylic acid ethyl ester derivatives of formula 6 by reacting 4-chloro-2-methylthio-5-pyrimidinecarboxylic acid ethyl ester of formula 4 with 5-aminoindazole or 6-aminoindazole of formula 5 (5represents compounds of both formula 2and formula 3; referred as formula 5 hereinafter) in a proper solvent under a basic condition at an appropriate temperature (step 1);
2-A) Preparation of 5-pyrimidinecarboxamide derivatives of formula 1 by reacting the compound of formula 6 prepared in step 1 with amine compound of formula 7 in an appropriate solvent at a proper temperature, or 5-aminoindazole or 6-aminoindazole of formula 5 to synthesize 5-pyrimidinecarboxylic acid ethyl ester derivatives of formula 6, organic compound may be used as a base. It is preferable to use tertiary amine such as triethylamine, N,N-diisopropylethylamine, N-methylmorpholine, N-methylpiperidine, 4-dimethylaminopyridine, N,N-dimethylaniline, 2,6-lutidine, pyridine.

Preferable reaction temperature is 20~40° C. and preferable reaction time is 1~6 hrs.

Preferable is a single solvent or a mixture of solvents selected from alcohol such as methanol and ethanol, chloroform, methylene chloride, and acetonitrile.

Preparation of 5-pyrimidinecarboxamide derivatives of formula 1 by reacting 5-pyrimidinecarboxylic acid ethyl ester derivatives of formula 6 synthesized in step 1 with amine compound of formula 7 may be carried out using one of two methods.

As in step 2-A, an appropriate amine compound of formula 7 may be used to give good yield of 5-pyrimidinecarboxamide derivatives of formula 1 without first going through the hydrolysis of aminoindazole 5-pyrimidinecarboxylic acid ethyl ester of formula 6.

In this case, amine compound of formula 7 is used to introduce substituents $R_1$ and $R_2$ and an appropriate amine may be selected depending on the kind of substituents desired. For amine compound, methanolic ammonia solution, methanolic methylamine solution, aqueous ethylamine solution, isopropylamine, cyclopropylamine, ethanolamine, or propanolamine are used all of which are commercially available.

For a base, organic base such as used in preparing compounds of formula 6 is used preferably in excess amount compared with that of intermediate of formula 7 in order to increase the reaction efficiency.

For a solvent, a single or a mixture of solvents selected from alcohol such as $H_2O$, methanol, ethanol, and isopropanol or chloroform, methylene chloride, and acetonitrile is preferable.

The reaction temperature is preferably 25~60° C. and may depend on the amine compound used.

As for the reaction in step 2-B, alkali compound used for hydrolyzing the compound of formula 6 is preferably sodium hydroxide, potassium hydroxide, sodium carbonate, or potassium carbonate. 5-Pyrimidinecarboxylic acid derivatives are formed almost quantitatively in the hydrolysis reaction.

For a solvent in this reaction, a mixture of water and alcohol such as methanol or ethanol is preferably used.

Preferable reaction temperature and time are 30~60° C. and 0.5~3 hrs.

5-pyrimidinecarboxylic acid derivatives are activated using Vilsmeier reagent formed by heating N,N-dimethylformamide and thionyl chloride at 30~50° C. and used in the reaction with an appropriate amine compound of formula 7 at 0~20° C. to prepare 5-pyrimidinecarboxamide derivatives of formula 1, target compound of the present invention.

For a solvent in this reaction, aprotic solvent is preferable such as chloroform, methylene chloride, acetonitrile, tetrahydrofuran, or ether.

Furthermore, the present invention provides the pharmaceutical compositions of therapeutics containing 5-pyrimidinecarboxamide derivatives and their pharmaceutically acceptable salts of formula 1 as effective ingredients to prevent and treat hepatitis B.

The present invention also provides the pharmaceutical compositions of therapeutics with 5-pyrimidinecarboxamide derivatives and their pharmaceutically acceptable salts of formula 1 as effective ingredients to prevent and treat AIDS.

5-pyrimidinecarboxamide derivatives of formula 1 in this invention are effective inhibitors in proliferation of HIV as well as of HBV, since they interfere with removal of RNA strand from RNA-DNA hybrid formed during reverse transcription of viral RNA to DNA which is common in the replication processes for HBV and HIV.

Compounds of formula 1 may be taken orally as well as through other routes in clinical uses; for example, it may be administered intravenously, subcutaneously, intraperitoneally, or locally and used in the form of general drugs.

For the clinical use of drugs with the pharmaceutical compositions of the present invention, compounds of formula 1 may be mixed with pharmaceutically acceptable excipients and made into various pharmaceutically acceptable forms; for example, tablets, capsules, trochise, solutions, suspensions for oral administration; and injection solutions, suspensions, or dried powder to be mixed with distilled water for the formulation of instant injection solution.

Effective dosage for compounds of formula 1 is generally 10~500 mg/kg, preferably 50~300 mg/kg for adults, which may be divided into several doses, preferably into 1~6 doses per day and administered if deemed appropriate by a doctor or a pharmacist.

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

PREPARATION EXAMPLE 1

Preparation of 4-(1H-5-Indazolylamino)-2-methylthio-5-pyrimidinecarboxilic Acid Ethyl Ester To the solution of 4-chloro-2-methylthio-5-pyrimidine carboxylic acid ethyl ester (5 g) and 5-aminoindazole (3.15 g) in methanol (70 ml) was added triethylamine (3.5 ml), and then the solution was reacted at 30° C. for 3 hr. The reaction mixture was cooled at room temperature, stirred at 20° C. for 1 hr. Then the reaction mixture was filtered and washed with methanol (20 ml). The obtained solid was dried at 40–50° C. in vacuo to obtain the desired compound (6.15 g, 87%).

m.p.: 199–201° C. $^1$H-NMR (DMSO-$d_6$), ppm: δ 1.34(t, 3H), 2.42(s, 3H), 4.34(m, 2H), 7.48(d, 1 H), 7.53(d, 1H), 8.06(d, 2H), 8.70(s, 1H), 10.18(s, 1H), 13.10(br s, 1H)

PREPARATION OF EXAMPLE 2

Preparation of 4-(1H-6-Indazolylamino)-2-methylthio-5-pyrimidinecarboxylic Acid Ethyl Ester To the solution of 4-chloro-2-methylthio-5-pyrimidine carboxylic acid ethyl ester (5 g) and 6-aminoindazole (3.15 g) in methanol (70 ml) was added N,N-diisopropylethylamine (4.2 ml), and then the solution was reacted at 30–35° C. for 4 hr. The reaction mixture was cooled, and then stirred at 20° C. for 1 hr. The reaction mixture was filtered, washed with methanol (20 ml) and dried at 40–50° C. in vacuo to obtain the desired compound (5.8 g, 82%).

m.p.: 212–214° C. $^1$H-NMR (DMSO-$d_6$), ppm: δ 1.33(t, 3H), 2.53(s, 3H), 4.33(m, 2H), 7.10(d, 1H), 7.70(d, 1H), 8.00(s, 1H), 8.22(s, 1H), 8.72(s, 1H), 10.40(s, 1H), 13.09(br s, 1H)

PREPARATION OF EXAMPLE 3

Preparation of 4-(1H-5-Indazolylamino)-2-methylthio-5-pyrimidinecarboxylic Acid

To the solution of methanol (80 ml) was added the 4-(1H-5-indazolylamino)-2-methylthio-5-pyrimidinecarboxylic acid ethyl ester (5 g) obtained by the preparation example 1, and the solution was hydrolyzed at 40–50° C. for 1 hr, adding H$_2$O (30 ml) and 3N aq. NaOH (15 ml). The reaction mixture was cooled, measured pH 5 at 20° C., slowly adding 3 N aq. HCl. And then the reaction mixture was slowly added H$_2$O (100 ml), stirred at 20° C. for 1 hr, filtered, washed with H$_2$O (30 ml), and obtained a solid product. The solid product was dried at 50° C. in vacuo to obtain the desired compound (4.44 g, 97%).

m.p.: >270° C. $^1$H-NMR (DMSO-d$_6$), ppm: δ 2.45(s, 3H), 7.49(d, 1H), 7.53(d, 1H), 8.05(s, 1H), 8.10(s, 1H), 8.68(s, 1H), 10.50(s, 1H), 13.09(br s, 1H)

PREPARATION OF EXAMPLE 4

Preparation of 4-(1H-6-Indazolylamino)-2-methylthio-5-pyrimidinecarboxylic Acid

The desired compound (95%) was obtained the same method used for the preparation of example 3, except using 4-(1H-5-indazolylamino)-2-methylthio-5-pyrimidinecarboxylic acid ethyl ester (5 g) prepared from preparation example 2 as a starting.

m.p.: >270° C. $^1$H-NMR (DMSO-d$_6$), ppm: δ 2.56(s, 3H), 7.10(d, 1H), 7.72(d, 1H), 8.01(s, 1H), 8.25(s, 1H), 8.73(s, 1H), 10.81(br s, 1H), 13.06(br s, 1H)

EXAMPLE 1

Preparation of 4-(1H-5-Indazolylamino)-2-methyl thio-5-pyrimidinecarboxamide

To the solution of 4-(1H-5-indazolylamino)-2-methylthio-5-pyrimidinecarboxilic acid ethylester (1 g) prepared from preparation example 1 in chloroform (10 ml) was added 10% ammonia methanol solution (20 ml), the solution was slowly heated and then reacted at 40° C. for 2 days. The reaction mixture was concentrated by evaporation under pressure crystallized by adding methanol (15 ml). The reaction mixture containing solid product was stirred at 20° C., filteres and then seperated a solid product. The solid product was recrystallized chloroform:ethanol=1:1(v/v) and dried in vacuo to obtain the desired compound (0.62 g, 68%).

m.p.: >270° C. $^1$H-NMR (DMSO-d$_6$), ppm: δ 2.49(s, 3H), 7.47(d, 1H), 7.55(d, 1H), 7.73(br s, 1H), 8.07(s, 1H), 8.15(s, 1H), 8.28(br s, 1H), 8.71(s, 1H), 11.46(s, 1H), 13.07(br s, 1H)

EXAMPLE 2

Preparation of 4-(1H-6-Indazolylamino)-2-methylthio-5-pyrimidinecarboxamide

The desired compound (62%) was obtained the same method used for the example 1, except using 4-(1H-6-indazolylamino)-2-methylthio-5-pyrimidinecarboxylic acid ethyl ester prepared from preparation example 2 as a starting. $^1$H-NMR (DMSO-d$_6$), ppm: δ 2.56(s, 3H), 7.06(d, 1H), 7.70(d, 1H), 7.81(br s, 1H), 7.98(s, 1H), 8.28(s, 1H), 8.32(br s, 1H, 8.73(s, 1H), 11.75(s, 1H), 13.02(br s, 1H)

EXAMPLE 3

Preparation of 4-(1H-5-Indazolylamino)-N-methyl-2-methylthio-5-pyrimidine carboxamide To the solution of methanol with 40% methylamine (30 ml) was added 4-(1H-5-indazolylamino)-2-methylthio-5-pyrimidine carboxylic acid ethyl ester (1.5 g) obtained by by preparation example 1, and the solution was reacted at 25–30° C. for 1 hr. The reaction mixture was cooled at 20–25° C., added H2O (90 ml) and stirred for 0.5hr. The reaction mixture was filtered, washed with 25% aqueous methanol solution (10 ml), obtained a solid product. The solid product was dried in vacuo to obtain the desired compound (1.26 g, 88%).

m.p.: 259~261° C. $^1$H-NMR (DMSO-d$_6$), ppm: δ 2.46(s, 3H), 2.80(d, 3H), 7.45(d, 1H), 7.52(d, 1H), 8.03(s, 1H), 8.13(s, 1H), 8.61(s, 1H), 8.75(br s, 1H), 11.28(s, 1H), 13.06(br s, 1H)

EXAMPLE 4

Preparation of 4-(1H-6-Indazolylamino)-N-methyl-2-methylthio-5-pyrimidinecarboxamide The desired compound (92%) was obtained the same method used for the example 3, except using 4-(1H-6-indazolylamino)-2-methylthio-5-pyrimidinecarboxylic acid ethyl ester prepared from preparation example 2 as a starting.

m.p.: 263~265° C. $^1$H-NMR (DMSO-d6), ppm: δ 2.56(s, 3H), 2.81(d, 3H), 7.05(d, 1H), 7.69(d, 1H), 7.98(s, 1H), 8.28(s, 1H), 8.67(s, 1H), 8.79(br s, 1H), 11.57(s, 1H), 13.02(br s, 1H)

EXAMPLE 5

Preparation of N-ethyl-4-(1H-5-Indazolylamino)-2-methylthio-5-pyrimidinecarboxamide To the solution of methanol (20 ml) was added 4-(1H-5-indazolylamino)-2-methylthio-5-pyrimidinecarboxylic acid ethyl ester (1 g) prepared from preparation example 1, added 70% aq. ethylamine (25ml) at room temperatute, and reacted at 30–35° C. for 3 hr. The reaction mixture was cooled and slowly added H$_2$O (30 ml) and stirred for 0.5 hr. The reaction mixture was filtered, washed with 30% aqueous methanol solution (10 ml) obtained the desired compound (0.8 g, 80%)

m.p.: 252~254° C. $^1$H-NMR (DMSO-d$_6$), ppm: δ 1.17(t, 3H), 2.49(s, 3H), 3.33(m, 2H), 7.48(d, 1H), 7.55(d, 1H), 8.07(s, 1H), 8.15(s, 1H), 8.65(s, 1H), 8.78(br s, 1H), 11.29(s, 1H), 13.09(br s, 1H)

EXAMPLE 6

Preparation of N-cyclopropyl-4-(1H-6-Indazolylamino)-2-methylthio-5-pyrimidinecarboxamide To the solution of methanol (20 ml) was added 4-(1H-6-indazolylamino)-2-methylthio-5-pyrimidinecarboxylic acid ethyl ester (1g) prepared from preparation example 2, added cyclopropylamine (7 ml) at room temperature, and reacted at 50° C. for 6 hr. The reaction mixture was cooled, and stirred at 25° C. for 0.5 hr with slowly adding H$_2$O (20 ml). The reaction mixture was filtered, washed with 30% aqueous methanol solution (10 ml), obtained the desired compound (0.67 g, 65%)

m.p.: >270° C. $^1$H-NMR (DMSO-d$_6$), ppm: δ 0.54(m, 2H), 0.67(m, 2H), 2.49(s, 3H), 2.78(m, 1H), 7.00(d, 1H), 7.63(d, 1H), 7.92(s, 1H), 8.21(s, 1H), 8.58(s, 1H), 8.69(br s, 1H), 11.46(s, 1H), 12.97(br s, 1H)

EXAMPLE 7

Preparation of N-(2-Hydroxyethyl)-4-(1H-5-indazolylamino)-2-methylthio-5-pyrimidinecarboxamide To the solution of methanol (20 ml) was added 4-(1H-5-indazolylamino)-2-methylthio-5-pyrimidinecarboxylic acid ethyl ester (1 g) prepared from preparation example 1, added ethanol amine (7 ml) at room temperature, and refluxed for 4 hr. The reaction mixture was cooled and slowly added H$_2$O (40 ml) at 20° C. and stirred for 0.5 hr. The reaction mixture was filtered, washed with 25% aqueous methanol solution (10 ml), obtained the desired compound (0.75 g, 72%)

m.p: >270° C. $^1$H-NMR (DMSO-d$_6$), ppm: δ 2.45(s, 3H), 3.36(m, 2H), 3.55(m, 2H), 4.81(m, 1H), 7.47(d, 1H), 7.54(d, 1H), 8.06(s, 1H), 8.15(s, 1H), 8.71(s, 1H), 8.77(br s, 1H), 11.25(s, 1H), 13.07(br s, 1H)

EXAMPLE 8

Preparation of N-(2-hydroxyethyl)-4-(1H-6-indazolylamino)-2-methylthio-5-pyrimidine Carboxamide The desired compound (76%) was obtained the same method used for the example 7, except using 4-(1H-6-indazolylamino)-2-methylthio-5-pyrimidinecarboxylic acid ethyl ester prepared from preparation example 2.

m.p: 269~270° C. $^1$H-NMR (DMSO-d$_6$), ppm: δ 2.56(s, 3H), 3.33(m, 2H), 3.54(m, 2H), 4.79(m, 1H), 7.04(d, 1H), 7.69(d, 1H), 7.98(s, 1H), 8.27(s, 1H), 8.72(s, 1H), 8.81(br s, 1H), 11.52(s, 1H), 13.03(br s, 1H)

EXAMPLE 9

Preparation of N-hydroxyethyl-N-methyl-4-(1H-5-indazolylamino)-2-methylthio-5-pyrimidine Carboxamide To the solution of methylene chloride (120 ml) was added N,N-dimethylformamide (1.1 ml) and thionyl chloride (1.2 ml) and refluxed for 2 hr. The solution was added 4-(1H-5-indazolylamino)-2-methylthio-5-pyrimidinecarboxylic acid ethyl ester (3 g) prepared from preparation example 3, and refluxed for 10 hr. The reaction mixture was cooled and slowly added 2-(methylamino)ethanol (4 ml) at 0~5° C. and stirred for 1 hr. The reaction mixture was added methanol (80 ml), stirred 5 min. and then filtered for removing impurity. The filtrate was concentration by evaporation under pressure and it was obtained a solid product. The solid product in methanol: H$_2$O=1:1 was added aq. 3N NaOH (3 ml), stirred for 1 hr, filtered and washed with H$_2$O. The desired compound (1.61 g. 45%) was obtained by recrystallization with methylene chloride:isopropyl ether=1:4.

m.p: 106~114° C. $^1$H-NMR (DMSO-d$_6$), ppm: δ 2.40(s, 3H), 2.99(s, 3H), 3.43(br s, 2H), 3.56(br s, 2H), 7.44(d, 1H), 3.50(d, 1H), 7.93(br s, 1H), 8.03(s, 1H), 8.14(s, 1H), 8.93(br s, 1H), 13.03(br s 1).

It was prepared compounds in prepared example 10~35 as the same method used for the example 9. It is shown in Table 1 that the compound name, yield, recrystallizing solution, melting point of compounds in prepared example 10~35 and 5-pyrimidinecarboxylic acid derivatives (8) and amine compound (7) as starting materials. It is shown in Table 2 that $^{1H}$-NMR of compounds in prepared example 10~35.

TABLE 1a

| Example | Compounds | | | | |
|---|---|---|---|---|---|
| | 5-pyrimidine carboxamide derivatives (8) | amine compound (7) | Recrystallizing soln | Yield (%) | m.p. (° C.) |
| 10 | N-hydroxyethyl-N-methyl-4-(1H-6-indazolylamino)-2-methylthio-5-pyrimidinecarboxamide | | | | |
| | Preparation example 4 | 2-(methyl-amino)ethanol | Chloroform/ isopropyl ether (1:4) | 52 | 93~97 |
| 11 | N-[(1R-1-(hydroxymethyl)propyl]-4-(1H-5-indazolylamino)-2-methylthio-5-pyrimidinecarboxamide | | | | |
| | Preparation example 3 | (R)-2-amino-i-buthanol | Methanol/ chloroform/ isopropyl ether (1:2:10) | 44 | 219~222 |
| 12 | N-[(1R)-1-(hydroxymethyl)propyl]-4-(1H-6-indazolylamino)-2-methylthio-5-pyrimidinecarboxamide | | | | |
| | Preparation example 4 | (R)-2-amino-1-buthanol | Methanol/ isopropyl ether (1:5) | 65 | 234~237 |
| 13 | 4-(1H-5-indazolylamino)-N-(2-methoxyethyl)-2-methylthio-5-pyrimidinecarboxamide | | | | |
| | Preparation example 3 | 2-methoxy-ethylamine | Acetone/ isopropyl ether (1:4) | 72 | 214~217 |
| 14 | 4-(1H-6-indazolylamino)-N-(2-methoxyethyl)-2-methylthio-5-pyrimidinecarboxamide | | | | |
| | Preparation example 4 | 2-methoxy-ethylamine | acetone/ isopropyl ether (1:4) | 75 | 225–228 |
| 15 | N,N-dimethyl-4-(1H-5-indazolylamino)-2-methylthio-5-pyrimidinecarboxamide | | | | |
| | Preparation example 3 | dimethylamine ethanol soln (33%) | methanol/ ethylacetate/ hexane (1:5:5) | 41 | 101–105 |
| 16 | N,N-dimethyl-4-(1H-6-indazolylamino)-2-methylthio-5-pyrimidinecarboxamide | | | | |
| | Preparation example 4 | dimethylamine ethanol soln (33%) | Methanol/ ethylacetate/ hexane (1:5:5) | 38 | 164–166 |
| 17 | N-[2-(dimethylamino)ethyl]-4-(1H-5-indazolylamino)-2-methylthio-5-pyrimidinecarboxamide | | | | |
| | Preparation example 3 | N,N-dimethyl-ethylene-diamine | chloroform/ ether/ methanol (3:3:1) | 43 | 111–114 |
| 18 | N-[2-(dimethylamino)ethyl]-4-(1H-6-indazolylamino)-2-methylthio-5-pyrimidinecarboxamide | | | | |
| | Preparation example 4 | N,N-dimethyl-ethylene-diamine | chloroform/ ether/ methanol (3:3:1) | 35 | 162–167 |
| 19 | 4-(1H-5-indazolylamino)-2-methylthio-N-[2-(4-morpholinyl)ethyl]-5-pyrimidinecarboxamide | | | | |
| | Preparation example 3 | 4-(2-amino-ethyl)-morpholine | chloroform/ ether/ methanol (3:3:1) | 52 | 113–117 |

TABLE 1b

| Example | Compounds | | | | |
|---|---|---|---|---|---|
| | 5-pyrimidine carboxylic derivatives (8) | amine compound (7) | Recrystallizing soln | Yield (%) | m.p. (° C.) |
| 20 | 4-(1H-6-indazolylamino)-2-methylthio-N-[2-(4-morpholinyl)ethyl[-5-pyrimidinecarboxamide | | | | |
| | Preparation example 4 | 4-(2-amino-ethyl) morpholine | Chloroform/ ether/ methanol (3:3:1) | 56 | 226–228 |

TABLE 1b-continued

Compounds

| Example | 5-pyrimidine carboxylic derivatives (8) | amine compound (7) | Recrystallizing soln | Yield (%) | m.p. (° C.) |
|---|---|---|---|---|---|
| 21 | 4-(1H-5-indazolylamino)-N-(4-methyl-1-piperazinyl)-2-methylthio-5-pyrimidinecarboxamide | | | | |
| | Preparation example 3 | 1-amino-4-methyl-piperazine | methylene chlroride/hexane (1:4) | 64 | 251–253 |
| 22 | 4-(1H-6-indazolylamino)-N-(4-methyl-1-piperazinyl)2-methylthio-5-pyrimidinecarboxamide | | | | |
| | Preparation example 4 | 1-amino-4-methyl-piperazine | methylene chlroride/hexane (1:4) | 53 | 244–247 |
| 23 | 4-(1H-5-indazolylamino)-N-[(1S)-1-(methoxycarbonyl)-(2R)-2-hydroxypropyl]-2-methylthio-5-pyrimidinecarboxamide | | | | |
| | Preparation example 3 | L-treonine-methyl ester | methanol | 76 | 227–232 |
| 24 | 4-(1H-6-indazolylamino)-N-[(1S)-1-(methoxycarbonyl)-(2R)-2-hydroxypropyl]-2-methylthio-5-pyrimidinecarboxamide | | | | |
| | Preparation example 4 | L-treonine-methyl ester | methanol | 78 | 226–228 |
| 25 | 4-(1H-5-indazolylamino)-2-methylthio-N-(3-pyridyl)methyl-5-pyrimidinecarboxamide | | | | |
| | Preparation example 3 | 3-(amino-methyl)-pyridine | methanol/ether (1:3) | 62 | 268–270 |
| 26 | 4-(1H-6-indazolylamino)-2-methylthio-N-(3-pyridyl)methyl-5-pyrimidinecarboxamide | | | | |
| | Preparation example 4 | 3-(amino-methyl)-pyridine | methanol/ether (1:3) | 74 | 253–256 |
| 27 | 4-(1H-5-indazolylamino)-2-methylthio-N-[2-(2-pyridyl)ethyl]-5-pyrimidinecarboxamide | | | | |
| | Preparation example 3 | 2-(2-amino-ethyl)-pyridine | methylene chloride/ether (1:2) | 49 | 220–223 |
| 28 | 4-(1H-6-indazolylamino)-2-methylthio-N-[2-(2-pyridyl)ethyl]-5-pyrimidinecarboxamide | | | | |
| | Preparation example 4 | 2-(2-amino-ethyl)-pyridine | methylene chloride/ether (1:2) | 56 | 230–231 |

TABLE 1c

Compounds

| Example | 5-pyrimidine carboxylic derivatives (8) | amine compound (7) | Recrystallizing soln | Yield (%) | m.p. (° C.) |
|---|---|---|---|---|---|
| 29 | N-[3-(1H-1-imidazolyl)propyl]-4-(1H-5-indazolylamino)-2-methylthio-5-pyrimidinecarboxamide | | | | |
| | Preparation example 3 | 1-(3-amino-propyl)-imidazole | chloroform/isopropyl ether (1:3) | 53 | 121–125 |
| 30 | N-[3-(1H-1-imidazolyl)propyl]-4-(1H-6-indazolylamino)-2-methylthio-5-pyrimidinecarboxamide | | | | |
| | Preparation example 4 | 1-(3-amino-propyl)-imidazole | methanol/ether (1:3) | 61 | 230–232 |
| 31 | 4-(1H-5-indazolylamino)-5-[(4-methyl-1-piperazinyl)-carbonyl]-2-methylthiopyrimidine | | | | |
| | Preparation example 3 | 1-methyl-piperazine | methylene chlroride/isopropyl-ether (1:2) | 57 | 153–155 |

TABLE 1c-continued

Compounds

| Example | 5-pyrimidine carboxylic derivatives (8) | amine compound (7) | Recrystallizing soln | Yield (%) | m.p. (° C.) |
|---|---|---|---|---|---|
| 32 | 4-(1H-6-indazolylamino)-5-[(4-methyl-1-piperazinyl)-carbonyl]-2-methylthiopyrimidine | | | | |
| | Preparation example 4 | 1-methyl-piperazine | methylene chlroride/isopropyl-ether (1:2) | 47 | 102–106 |
| 33 | 5-[[4-(2-hydroxyethyl)-1-piperazinyl]carbonyl]-4-(1H-5-indazolylamino)-2-methylthiopyrimidine | | | | |
| | Preparation example 3 | 1-(2-hydroxy-ethyl)-piperazine | chloroform/isopropyl ether (1:3) | 58 | 166–170 |
| 34 | 5-[[4-(2-hydroxyethyl)-1-piperazinyl]carbonyl]-4-(1H-6-indazolylamino)-2-methylthiopyrimidine | | | | |
| | Preparation example 4 | 1-(2-hydroxy-ethyl)-piperazine | chloroform/isopropyl ether (1:3) | 52 | 114–117 |
| 35 | 4-(1H-5-indazolylamino)-2-methylthio-N-(4-morpholinyl)-5-pyrimidinecarboxamide | | | | |
| | Preparation example 3 | 4-amino-morpholine | methanol/H$_2$O (1:1) | 60 | 239–242 |

TABLE 2a

| Example | NMR solution | $^1$H-NMR data (ppm) |
|---|---|---|
| 10 | DMSO-d$_6$ | δ2.49(s, 3H), 3.00(s, 3H), 3.45(br s, 2H), 3.56(br s, 2H), 7.15 (d, 1H), 7.67 (d, 1H), 7.97 (s, 1H), 8.05 (br s, 1H), 8.22(s, 1H), 9.04(br s, 1H), 13.00(br s, 1H) |
| 11 | DMSO-d$_6$ | δ0.88(t, 3H), 1.45(m, 1H), 1.63(m, 1H), 2.47(s, 3H), 3.45(m, 2H), 3.89(br s, 1H), 7.49(m, 2H), 8.03(s, 1H), 8.12(s, 1H), 8.32(d, 1H), 8.71(s, 1H), 11.22(s, 1H), 13.03(br s, 1H) |
| 12 | DMSO-d$_6$ | δ0.88(t, 3H), 1.46(m, 1H), 1.65(m, 1H), 2.56(s, 3H), 3.43(m, 2H), 3.89(br s, 1H), 7.05(d, 1H), 7.70(d, 1H), 7.99(s, 1H), 8.28(s, 1H), 8.38(d, 1H), 8.77(s, 1H), 11.50(s, 1H), 12.99(br s, 1H) |
| 13 | DMSO-d$_6$ | δ2.46(s, 3H), 3.28(s, 3H), 3.46(m, 4H), 7.45(d, 1H), 7.52(d, 1H), 8.03(s, 1H), 8.12(s, 1H), 8.66(s, 1H), 8.84(br s, 1H), 11.22(s, 1H), 13.05(br s, 1H) |
| 14 | DMSO-d$_6$ | δ2.56(s, 3H), 3.27(s, 3H), 3.46(m, 4H), 7.05(d, 1H), 7.69(d, 1H), 7.99(s, 1H), 8.27(s, 1H), 8.71(s, 1H), 8.89(br s, 1H), 11.51(br s, 1H), 13.05(br s, 1H) |
| 15 | DMSO-d$_6$ | δ2.34(s, 3H), 2.92(s, 6H), 7.41(m, 2H), 7.86(d, 1H), 7.97(s, 1H), 8.07(d, 1H), 9.10(s, 1H), 12.96(br s, 1H), |
| 16 | DMSO-d$_6$ | δ2.49(s, 3H), 2.99(s, 6H), 7.16(d, 1H), 7.67(d, 1H), 7.97(s, 1H), 8.04(d, 1H), 8.20(s, 1H), 9.31(br s, 1H), 13.00(br s, 1H) |
| 17 | DMSO-d$_6$ | δ2.25(s, 6H), 2.52(m, 5H), 3.41(m, 2H), 7.48(d, 1H), 7.55(m, 1H), 8.06(s, 1H), 8.14(s, 1H), 8.65(s, 1H), 8.76(br s, 1H), 11.23(br s, 1H), 13.10(br s, 1H) |
| 18 | DMSO-d$_6$ | δ2.18(s, 6H), 2.42(m, 2H), 2.49(s, 3H), 3.36(m, 2H), 7.45(d, 1H), 7.52(d, 1H), 8.03(s, 1H), 8.11(s, 1H), 8.65(s, 1H), 8.76(br s, 1H), 11.22(br s, 1H), 13.08(br s, 1H) |
| 19 | DMSO-d$_6$ + TFA-d$_1$ | δ2.50(s, 3H), 3.14(t, 2H), 3.34(t, 2H), 3.54(d, 2H), 3.68(m, 4H), 3.96(d, 2H), 7.48(m, 1H), 7.58(d, 1H), 8.06)t, 2H), 8.71(s,1H) |
| 20 | DMSO-d$_6$ | δ2.36(s, 4H), 2.49(s, 3H), 3.26(s, 2H), 3.34(d, 2H), 3.50(s, 4H), 6.97(d, 1H), 7.63(d, 1H), 7.91(s, 1H), 8.20(s, 1H), 8.61(s, 1H), 8.71(br s, 1H), 11.41(s, 1H) 12.97(br s, 1H) |

TABLE 2a-continued

| Example | NMR solution | ¹H-NMR data (ppm) |
|---|---|---|
| 21 | DMSO-$d_6$ + TFA-$d_1$ | δ2.37(s, 3H), 2.82(s, 3H), 3.13–3.22(m, 6H), 3.49(d, 2H), 7.49(d, 1H), 7.57(d, 1H), 8.03(s, 1H), 8.07(s, 1H), 8.67(s, 1H) |
| 22 | DMSO-$d_6$ + TFA-$d_1$ | δ2.58(s, 3H), 2.82(s, 3H), 3.13–3.25(m, 6H), 3.47(d, 2H), 7.13(d, 1H), 7.73(d, 1H), 8.06(s, 1H), 8.18(s, 1H), 8.69(s, 1H) |

DMSO: dimethylsulfoxide, TFA: trifluoroacetic acid

TABLE 2b

| Example | NMR solution | ¹H-NMR data (ppm) |
|---|---|---|
| 23 | DMSO-$d_6$ | δ1.16(d, 3H), 2.47(s, 3H), 3.68(s, 3H), 4.19(m, 1H), 4.50(br s, 1H), 5.03(d, 1H), 7.45(d, 1H), 7.52(d, 1H), 8.04(s, 1H), 8.10(s, 1H), 8.71.(d, 1H), 8.80(s, 1H), 10.86(s, 1H), 13.06(br s, 1H) |
| 24 | DMSO-$d_6$ | δ1.16(d, 3H), 2.56(s, 3H), 3.68(s, 3H), 4.19(m, 1H), 4.51(br s, 1H), 5.04(d, 1H), 7.05(d, 1H), 7.69(d, 1H), 7.99(s, 1H), 8.25(s, 1H), 8.77(d, 1H), 8.85(s, 1H), 11.11(br s, 1H), 13.05(br s, 1H) |
| 25 | DMSO-$d_6$ | δ2.54(s, 3H), 4.60(d, 2H), 7.44(m, 1H), 7.52(d, 1H), 7.59(d, 1H), 7.84(d, 1H), 8.11(d, 1H), 8.19(d, 1H), 8.54(d, 1H), 8.66(s, 1H), 8.78(d, 1H), 9.43(br s, 1H), 11.23 (s, 1H), 13.13(br s, 1H) |
| 26 | DMSO-$d_6$ | δ2.56(s, 3H), 4.53(d, 2H), 7.05(m, 1H), 7.37(m, 1H), 7.69(d, 1H), 7.77(m, 1H), 7.98(s, 1H), 8.27(s, 1H), 8.47(m, 1H), 8.59(d, 1H), 8.77(s, 1H), 9.41(t, 1H), 11.43(br s, 1H), 13.03(br s, 1H) |
| 27 | DMSO-$d_6$ | δ2.47(s, 3H), 3.01(t, 2H), 3.63(t, 2H), 7.22(t, 1H), 7.29(d, 1H), 7.45(d, 1H), 7.52(d, 1H), 7.71(t, 1H), 8.04(s, 1H), 8.13(s, 1H), 8.51(s, 1H), 8.58(s, 1H), 8.86(s)br s, 1H), 11.17(br s, 1H), 13.06(br s, 1H) |
| 28 | DMSO-$d_6$ | δ2.56(s, 3H), 3.01(t, 2H), 3.64(t, 2H), 7.05(d, 1H), 7.22(t, 1H), 7.30(d, 1H), 7.70(d, 2H), 7.99(s, 1H), 8.27(s, 1H), 8.50(s, 1H), 8.63(s, 1H), 8.92(br s, 1H), 11.47(br s, 1H), 13.03(br s, 1H) |
| 29 | DMSO-$d_6$ | δ1.98(t, 2H), 2.47(s, 3H), 3.24(t, 2H), 4.04(t, 2H), 6.88(s, 1H), 7.21(s, H), 7.45(d, 1H), 7.52(d, 1H), 7.66(s, 1H), 8.03(s, 1H), 8.13(s, 1H), 8.65(s, 1H), 8.76(br s, 1H), 11.12(br s, 1H), 13.05(br s, 1H) |
| 30 | DMSO-$d_6$ | δ1.98(m, 2H), 2.57(s, 3H), 3.26(m, 2H), 4.04(t, 2H), 6.89(s, 1H), 7.05(d, 1H), 7.21(s, 1H), 7.69(t, 2H), 7.98(s, 1H), 8.28(s, 1H), 8.69(s, 1H), 8.81(s, 1H), 11.43(br s, 1H), 13.06(br s, 1H) |
| 31 | DMSO-$d_6$ + TFA-$d_1$ | δ2.48(s, 3H), 2.82(s, 3H), 3.06(t, 2H), 3.31(br s, 2H), 3.47(d, 2H), 4.26(br s, 2H), 7.45(d, 1H), 7.56(d, 1H), 7.87(s, 1H), 8.06(s, 1H), 8.31(s, 1H) |
| 32 | DMSO-$d_6$ + TFA-$d_1$ | δ2.44(s, 3H), 2.77(s, 3H), 3.00(t, 2H), 3.25(br s, 2H), 3.42(d, 2H), 4.24(br s, 2H), 7.18(d, 1H), 7.69(d, 1H), 7.86(s, 1H), 8.00(s, 1H), 8.30(s, 1H) |
| 33 | DMSO-$d_6$ | δ2.39(t, 5H), 2.49(d, 4H), 3.48(m, 6H), 4.13(t, 1H), 7.44(d, 1H), 7.49(d, 1H), 7.92(d, 1H), 8.02(s, 1H), 8.08(s, 1H), 9.11(s, 1H), 13.02(br s, 1H) |
| 34 | DMSO-$d_6$ + TFA-$d_1$ | δ2.45(s, 3H), 3.14(d, 4H), 3.49(br s, 4H), 3.72(s, 2H), 4.22(br s, 2H), 7.22(d, 1H), 7.71(d, 1H), 7.89(s, 1H), 8.05(s, 1H), 8.34(s, 1H) |
| 35 | DMSO-$d_6$ | δ2.53(s, 3H), 2.96(s, 4H), 3.74(s, 4H), 7.52(d, 1H), 7.59(d, 1H), 8.06(s, 1H), 8.19(s, 1H), 8.61(s, 1H), 9.83(s, 1H), 10.95(s, 1H), 13.12(br s, 1H) |

DMSO: dimethylsulfoxide, TFA: trifluoroacetic acid

EXPERIMENT 1
Inhibitory Effect on the In Vitro Activities of HBV Polymerase in Reverse Transcription The following in vitro experiment was performed to determine the effect of the compounds of formula 1 on the activity of HBV polymerase during reverse transcription.

The present inventors submitted application for a patent concerning HBV polymerase genetically expressed in and separated from E. coli, the process of its preparation, and the method to measure the enzyme activities (KR 94-3918, KR 96-33998). In the present experiments HBV polymerase was used which had been expressed in E. coli as stated above.

The method used in the present invention to measure in vitro reverse transcribing activities of HBV polymerase is as follows. Basic principles are the same as for ELISA. Nucleotides with biotin or digoxigenin group attached are included as substrates and anti-DIG antibodies attached to peroxidase enzyme recognize the polymerized substrates.

To the wells coated with streptavidin, 20 μl of HBV polymerase, 20 μl of reaction mixture (10 μM each of DIG-UTP and Biotin-UTP, 46 mM Tris-HCl, 266 mM KCl, 27.5 mM $MgCl_2$, 9.2 mM DTT substrate/primer hybrid), and 20 μl of test compound (added to 1, 0.1, and 0.01 μg/ml) were added and allowed to react a 22° C. for 15 hrs. During this reaction, HBV polymerase catalyzes DNA synthesis and digoxigenin and biotin attached to nucleotides form bonds with streptavidin coated on the bottom of wells. When the reaction was done, each well was washed with 250μl of cleaning buffer (pH 7.0) for 30 seconds, which was repeated five times to remove remaining impurities. 200 μl of anti-DIG-POD antibody was added to each well and allowed to react for 1 hr at 37° C., and the wells were washed with cleaning buffer to remove impurities. 200μl each of ABTS™, a substrate of peroxidase, was then added and allowed to react at room temperature for 30 min. Absorbance was measured at 405 nm using ELISA reader.

The percentage of reduction in HBV polymerase activities for reverse transcription was calculated using the group without test compound as a control and the results are shown in Table 3.

TABLE 3a

Effect on the HBV polymerase activities in reverse transription

| Compound | Inhibition activity on HBV-RT (%) | | |
|---|---|---|---|
| | 1 μg/ml | 0.1 μg/ml | 0.01 μg/ml |
| Example 1 | 90 | 63 | 40 |
| Example 2 | 85 | 55 | 36 |
| Example 3 | 88 | 59 | 34 |
| Example 4 | 96 | 77 | 52 |
| Example 5 | 70 | 52 | 20 |
| Example 6 | 74 | 43 | 24 |
| Example 7 | 93 | 76 | 48 |
| Example 8 | 95 | 68 | 50 |
| Example 9 | 75 | 54 | 30 |
| Example 10 | 70 | 48 | 22 |
| Example 11 | 82 | 59 | 44 |
| Example 12 | 85 | 55 | 36 |
| Example 13 | 58 | 40 | 13 |
| Example 14 | 60 | 42 | 25 |
| Example 15 | 77 | 61 | 42 |
| Example 16 | 54 | 30 | 10 |
| Example 17 | 80 | 51 | 15 |
| Example 18 | 92 | 66 | 54 |
| Example 19 | 64 | 39 | 10 |
| Example 20 | 67 | 40 | 12 |
| Example 21 | 78 | 54 | 40 |
| Example 22 | 72 | 46 | 28 |
| Example 23 | 51 | 40 | 18 |
| Example 24 | 82 | 63 | 50 |
| Example 25 | 97 | 76 | 53 |
| Example 26 | 98 | 79 | 55 |
| Example 27 | 88 | 60 | 48 |
| Example 28 | 95 | 70 | 52 |
| Example 29 | 80 | 56 | 41 |
| Example 30 | 91 | 58 | 32 |

TABLE 3b

Effect on the HBV polymerase activities in reverse transription

| | Inhibition activity on HBV-RT (%) | | |
|---|---|---|---|
| Compound | 1 µg/ml | 0.1 µg/ml | 0.01 µg/ml |
| Example 31 | 82 | 58 | 43 |
| Example 32 | 62 | 40 | 26 |
| Example 33 | 53 | 32 | 11 |
| Example 34 | 59 | 43 | 15 |
| Example 35 | 90 | 61 | 46 |

As shown in Table 3, compounds of the present invention have excellent inhibitory effects on the HBV polymerase activities with more than 70%, up to max. 98% inhibition at the concentration of 1 µg/ml. Moreover, compounds of the present invention are not expected to have problems such as toxicity and development of resistant viruses as observed in the use of nucleosides and may be applied together with nucleoside compounds due to different mechanisms of action.

In summary, compounds of the present invention effectively reduce the activities of HBV polymerase, inhibit replication and proliferation of HBV and may be useful as therapeutics for prevention and treatment of hepatitis B.

EXPERIMENT 1

Inhibitory Effect on the Proliferation of HBV in HBV Producing Cell Line

The following experiment was performed to determine inhibitory effects of compounds of formula on the proliferation of HBV producing cell line.

To test for antiviral effect, replication and proliferation of HBV were measured in HepG 2.2.15, a human liver cancer cell line.

The cell concentration was adjusted to $1 \times 10^5$ cells/ml and 1 ml was added to each well of a 24-well cell culture plate, which was then kept in a culture box for 3–4 days at 37° C. under 5% $CO_2$ until cells grew sufficiently, changing culture medium everyday. When the cells matured sufficiently, the test compounds were added to the final concentrations of 0.01, 0.1, and 1 µg/ml. One week after the addition of test compounds, he culture solution was centrifuged at 5,000 rpm for 10 min. 25 µl of supernatant was transferred to a new tube and 5 µl of lysis solution [0.54N NaOH, 0.06% NP40] was added to each tube. After keeping the tube at 37° C. for 1 hr, 30 µl . of neutralizing solution [0.09NHCl, 0.1MTris-HCl, pH7.4] was added as a reaction solution for competitive polymerase chain reaction (PCR).

PCR was performed using genetic sequence of HBV core protein as a matrix. PCR reaction was carried out by adding 1 unit of Taq polymerase enzyme to 25 pmol of each primer, 250 µM dNTP, 5 µl of PCR reaction solution [0.54N NaOH, 0.06% NP40, 0.09N HCl, 0.1M Tris-HCl, pH 7.4].

DNA polymerized by PCR was electrophoresed on Agarose gel and quantitatively analyzed using an image analyzer (Gel Dcc 1000, Bio-Rad) in order to evaluate the effect of compounds of the present invention on the reduction of HBV proliferation.

3TC (lamivudine) was used as a positive control at the same concentrations as those of the test compounds. The percentage of reduction in HBV proliferation was calculated using the group without test compound as a control and the results are represented in Table 4.

TABLE 4

Inhibitory effect on the HBV proliferation

| | Inhibition activity on HBV-RT (%) | | |
|---|---|---|---|
| Compound | 1 µg/ml | 0.1 µg/ml | 0.01 µg/ml |
| Example 1 | 82 | 53 | 25 |
| Example 2 | 70 | 40 | 20 |
| Example 3 | 75 | 42 | 15 |
| Example 4 | 94 | 70 | 32 |
| Example 7 | 92 | 61 | 21 |
| Example 8 | 88 | 72 | 40 |
| Example 9 | 65 | 48 | 20 |
| Example 15 | 70 | 52 | 25 |
| Example 18 | 88 | 57 | 43 |
| Example 25 | 92 | 65 | 40 |
| Example 26 | 97 | 75 | 47 |
| Example 27 | 84 | 55 | 38 |
| Example 28 | 93 | 68 | 44 |
| Example 35 | 86 | 50 | 29 |
| 3TC | 99 | 80 | 48 |

As shown above in Table 4, non-nucleoside compounds of the present invention have excellent inhibitory effect on the HBV polymerase activities in reverse transcription with more than 80%, up to max. 97% reduction of HBV proliferation at the concentration of 1 µg/ml. Moreover, compounds of the present invention, being non-nucleosides, may not have problems such as toxicity and early development of resistant virus strains observed in the use of nucleoside substances. It is also expected that compounds of the present invention may be used in parallel with nucleoside compounds since the former act on allosteric binding pockets while the latter act in the domain of polymerase activities.

As described above, compounds of the present invention have excellent inhibitory effect on the HBV polymerase activities important in reverse transcription step of HBV replication. Based on the mechanism, these compounds are able to effectively control HBV proliferation and may be useful as therapeutics for prevention and treatment of hepatitis B.

EXPERIMENT 3

Inhibitory Effect on the In Vitro HIV Enzyme Activities in Reverse Transcription The following in vitro experiments were done to determine the effect of compounds of formula 1 on the reduction of HIV enzyme activities in reverse transcription.

Non-radioactive reverse transcriptase assay kit (Boehringer Mannheim) was used in the measurement of in vitro transcriptase activities. 20 µl (40 ng) of HIV transcriptase and 20 µl of reaction mixture containing matrix-primer hybrid poly (A) oligo (dT) 15, DIG(digoxigenin)-dUTP, biotin-dUTP, and TTP were added to wells coated with streptavidin. Test compounds were also added at the final concentrations of 0.1 and 1 µg/ml and allowed to react at 37° C. for 1 hr. At this time, DNA is formed from RNA by the action of HIV transcriptase, forming bonds with streptavidin coated on the bottom of wells because of digoxigenin and biotin moieties attached to nucleotides.

When the reaction was completed, each well was washed with 250 μl. of cleaning buffer (pH 7.0) for 30 sec. five times to remove remaining impurities. 200 μl of anti-DIG-POD antigen was added to each well, allowed to react at 37° C. for 1 hr and washed as above to remove impurities. 200 μl of ABTS™, a substrate for peroxidase, was added to each well and allowed to react at room temperature for 30min. Absorbance at 405 nm was then read for each solution using ELISA reader and used for quantitative determination of inhibitory effect on the HIV transcriptase activities. The percentage of reduction in the activities of HIV reverse transcriptase was calculated using the group without test compound as control and the results are represented in Table 5.

TABLE 5

Inhibitory effect on the activities of HIV reverse transcriptase

| Compound | Inhibition activity on HBV-RT (%) | |
|---|---|---|
| | 1 μg/ml | 0.1 μg/ml |
| Example 1 | 65 | 44 |
| Example 3 | 62 | 48 |
| Example 4 | 70 | 42 |
| Example 5 | 80 | 57 |
| Example 6 | 78 | 54 |
| Example 9 | 84 | 52 |
| Example 10 | 80 | 47 |
| Example 16 | 81 | 53 |
| Example 18 | 77 | 51 |
| Example 19 | 75 | 48 |
| Example 20 | 89 | 50 |
| Example 29 | 72 | 44 |

As shown above in Table 5, compounds of the present invention have excellent inhibitory effect on the activities of HIV reverse transcriptase, having more than 80%, up to max. 89% reduction at the concentration of 1 μl/ml. Moreover, it is expected that compounds of the present invention, being non-nucleosidic, do not have problems such as toxicity and early development of resistant virus strains observed in the use of nucleoside substances. Furthermore, compounds of the present invention may be used together with nucleoside compounds since the former act on allosteric binding pockets while the latter act in the of polymerase activities.

As described above, compounds of the present invention have excellent inhibitory effect on the HIV enzyme activities in reverse transcription, which is a step in HIV replication. Based on the mechanism, these compounds are able to effectively control HIV proliferation and maybe useful as theraoeutics for prevention and treatment of AIDS.

EXPERIMENT 4

Cytotoxicity Test

To determine if compounds of formula 1 exhibit cytotoxicity, in vitro tests were carried out using HepG2cells with MTT analysis method as generally known and the results are in Table 6 shown below.

TABLE 6

Cytotoxicity tests on HepG2 cells

| Compound | Cytotoxity on HepG2 | |
|---|---|---|
| | $IC_{50}^1$ | $MCD^2$ |
| Example 3 | >100 | 100 |
| Example 4 | >100 | 100 |
| Example 8 | >100 | 100 |

[1]$IC_{50}$: 50% Inhibitory Concentration (μg/ml)
[2]MCD: Minimal Cytotoxic Concentration (μg/ml)

As shown above in Table 6, compounds used in the experiments have higher than 100 μg/ml for $IC_{50}$ and are considered to have little cytotoxicity.

EXPERIMENT 5

Acute Toxicity in Rats Tested Via Oral Administration

The following experiments were performed to see if compounds of formula 1 have acute toxicity in rats.

6-week old SPF SD line rats were used in the tests for acute toxicity. Compounds in the examples of 1~35 were suspended in 0.5% methylcellulose solution and orally administered once to 6rats per group at the dosage of 4g/kg/15 ml. Death, clinical symptoms, and weight change in rats were observed, hematological tests and biochemical tests of blood performed, and any abnormal signs in the gastrointestinal organs of chest and abdomen checked with eyes during autopsy. The results showed that the test compounds did not cause any specific clinical symptoms, weight change, or death in rats. No change was observed in hematological tests, biochemical tests of blood, and autopsy. The compounds used in this experiment are evaluated to be safe substances since they do not cause any toxic change in rats up to the level of 4 g/kg and their estimated $LD_{50}$ values are much greater than 4 g/kg in rats.

INDUSTRIAL APPLICABILITY

As described above, novel 5-pyrimidinecarboxamide derivatives of formula 1 in the present invention have dramatic inhibitory effect on proliferation of HBV and of HIV with little side effect and may be useful as therapeutic agents for prevention and treatment of hepatitis B and AIDS.

Moreover, it is expected that compounds of the present invention, being non-nucleosidic, do not have problems such as toxicity and early development of resistant virus strains observed in the use of nucleoside substances. Furthermore, compounds of the present invention may be used together with nucleoside compounds since the former seem to act on allosteric binding pockets while the latter work in the domain of polymerase activities.

What is claimed is:

1. 5-Pyrimidinecarboxamide compound or its pharmaceutically acceptable salt represented below in formula 1.

Formula 1

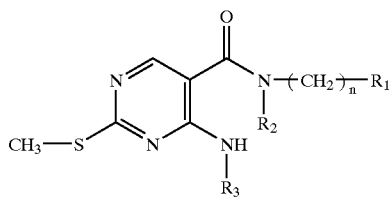

wherein, $R_1$ is H, hydroxy, straight or branched alkyl group with $C_1$~$C_5$, straight or branched alkoxy group with $C_1$~$C_5$, straight or branched hydroxyalkyl group with $C_2$~$C_6$, dialkylamino group with 2~6 carbons, straight or branched alkyl group with $C_3$~$C_6$ substituted with hydroxy or alkoxycarbonyl group with $C_2$~$C_5$, cycloalkyl group with $C_3$~$C_6$, or saturated or unsaturated 5 or 6 membered heterocyclic compounds containing 1 to 3 heteroatoms selected from N, O, and S, which may be unsubstituted or substituted with alkyl group of $C_1$~$C_3$; $R_3$ may or may not contain asymmetrical carbons;

$R_2$ is H or straight or branched alkyl group with $C_1$~$C_4$; or both $R_1$ and $R_2$ consist of 5 or 6 membered saturated heterocyclic ring containing 1~3 heteroatoms selected from N, O, and S, which is unsubstituted or substituted with straight or branched alkyl group with $C_1$~$C_5$ or straight or branched hydroxyalkyl group with $C_2$~$C_5$;

$R_3$ is indazol-5-yl or indazol-6-yl;

n is an integer between 0 and 4.

2. Process for preparing the 5-pyrimidinecarboxamide compound of claim 1, which comprises the following steps;

1) Preparation of 5-pyrimidinecarboxylic acid ethyl ester compound of formula 6 by reacting 4-chloro-2-methylthio-5-pyrimidinecarboxylic acid ethyl ester of formula 4 with 5-aminoindazole or 6-aminoindazole of formula 5 under a basic condition (step 1);

2-A) Preparation of 5-pyrimidinecarboxamide compound of formula 1 by reacting the compound of formula 6 with amine compound of formula 7, or 2-B) Preparation of 5-pyrimidinecarboxamide compound of formula 1 by first hydrolyzing the compound of formula 6 to form 5-pyrimidinecarboxylic acid compound of formula 8, and then activating to a Vilsmeier intermediate in the presence of N,N-dimethylformamide and $SOCl_2$, and allowing it to react with amine compound of formula 7 (step 2)

Scheme 1

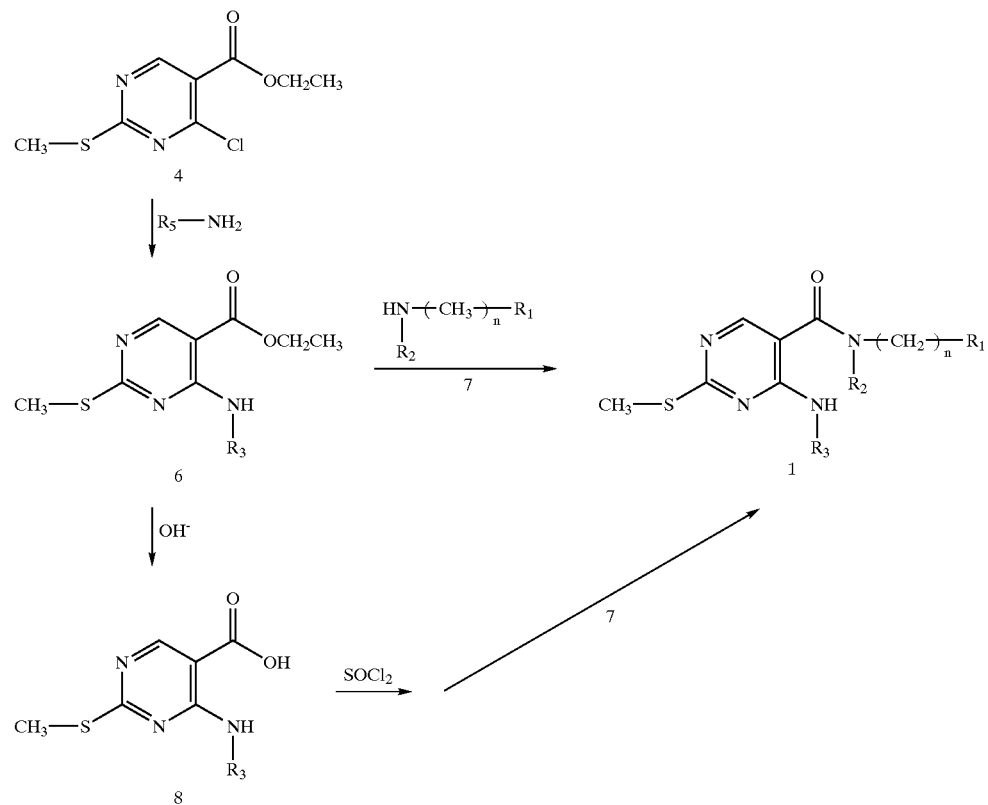

wherein, $R_1$, $R_2$, $R_3$, and n are as defined in claim 1.

3. A pharmaceutical composition for treating hepatitis B comprising an effective amount of the 5-pyrimidinecarboxamide compound or its pharmaceutically acceptable salt of claim 1, and a pharmaceutically acceptable excipient.

4. A pharmaceutical composition for treating acquired immune deficiency syndrome (AIDS) comprising an effective amount of the 5-pyrimidinecarboxamide compound or its pharmaceutically acceptable salt of claim 1, and a pharmaceutically acceptable excipient.

* * * * *